(12) United States Patent
Igaki et al.

(10) Patent No.: US 7,498,042 B2
(45) Date of Patent: Mar. 3, 2009

(54) STENT FOR BLOOD VESSEL AND MATERIAL FOR STENT FOR BLOOD VESSEL

(75) Inventors: Keiji Igaki, Kyoto (JP); Hideki Yamane, Shiga (JP)

(73) Assignee: Kyoto Medical Planning Co., Ltd., Kyoto (JP)

( * ) Notice: Subject to any disclaimer, the term of this patent is extended or adjusted under 35 U.S.C. 154(b) by 983 days.

(21) Appl. No.: 10/182,271

(22) PCT Filed: Aug. 8, 2001

(86) PCT No.: PCT/JP01/06831

§ 371 (c)(1),
(2), (4) Date: Oct. 25, 2002

(87) PCT Pub. No.: WO02/43799

PCT Pub. Date: Jun. 6, 2002

(65) Prior Publication Data

US 2003/0104030 A1 Jun. 5, 2003

(30) Foreign Application Priority Data

Nov. 30, 2000 (JP) .............................. 2000-365036

(51) Int. Cl.
*A61F 2/00* (2006.01)
*A61F 2/06* (2006.01)
*A61L 33/00* (2006.01)
*B05D 3/00* (2006.01)

(52) U.S. Cl. .................. 424/426; 424/422; 424/423; 424/424; 424/425; 623/1.11; 623/1.42; 623/1.44; 623/1.46; 623/1.49; 427/2.24; 427/2.25

(58) Field of Classification Search .................. 424/443, 424/422–426; 427/2.3, 2.25, 2.28; 623/1, 623/1.11, 1.42, 1.44, 1.46, 1.49; 247/2.24, 247/2.25
See application file for complete search history.

(56) References Cited

U.S. PATENT DOCUMENTS

| 4,598,006 | A | | 7/1986 | Sand |
| 5,464,650 | A | | 11/1995 | Berg et al. |
| 5,733,327 | A | * | 3/1998 | Igaki et al. ................. 623/1.5 |
| 6,153,252 | A | * | 11/2000 | Hossainy et al. ............. 427/2.3 |

FOREIGN PATENT DOCUMENTS

| JP | 11-500047 | 1/1999 |
| WO | 97/10011 | 3/1997 |

OTHER PUBLICATIONS

Kazarian, S. G. "Ploymer Processing with Supericritical Fluids" Polymer Science, Ser. C. vol. 42, No. 1 2000. pp. 78-101.

* cited by examiner

*Primary Examiner*—Michael G. Hartley
*Assistant Examiner*—Micah-Paul Young
(74) *Attorney, Agent, or Firm*—Rader, Fishman & Grauer, PLLC

(57) ABSTRACT

A luminal stent, implanted and implanted and left in the blood vessel, is disclosed. By permitting a stent (1), formed of a biodegradable polymer material (2), to be swollen, and by impregnating the swollen stent (1) with a drug, a sufficient quantity of the drug is impregnated in the stent. This drug is continuously released into the blood vessel over a prolonged time. A biodegradable polymer layer is formed on the surface of the stent (1) impregnated with the drug, and the release rate of the drug impregnated in the stent is controlled.

15 Claims, 5 Drawing Sheets

STENT FOR BLOOD VESSEL AND MATERIAL FOR STENT FOR BLOOD VESSEL

TECHNICAL FIELD

This invention relates to a luminal stent, introduced in the blood vessel. More particularly, it relates to a luminal stent in which a drug is impregnated into the material forming the stent.

BACKGROUND ART

In angioplasty, mechanical techniques such as balloon expansion or stent implantation is likely to damage the blood vessel. In a site of lesion of the blood vessel, acute closure, caused by thrombosis, or re-stenosis caused by intimal hyperplasia of the blood vessel, as a curative reaction of the blood vessel wall, occurs frequently.

The acute closure is correlated with thrombosis. For its prevention, an anti-thrombotic therapy is performed by systemic medication, usually through a vein.

On the other hand, re-stenosis is caused by excessive hyperplasia of cells. At present, researches into drugs suppressing this hyperplasia of cells are advancing rapidly, and several drugs have demonstrated satisfactory results.

However, deleterious side effects have been pointed out because systemic medication at a high concentration or in a large quantity is required in order to achieve the effect of these drugs.

For this reason, an LDDS (local drug delivery system) recently has been used as a safe and effective method for prevention of acute closure or re-stenosis. Several such LDDS-based methods have been proposed for implanting a catheter in the blood vessel to introduce the drug to a target site. With these methods, it is necessary to keep the catheter inserted continuously over a prolonged time in the blood vessel, therefore the blood flow is interrupted, so that sufficient effect of the drug is difficult to achieve and consequently none of the methods has been put to practical use.

For this reason, it is a stent that is now stirring up attention as an LDDS member for transporting the drug to a target side in the blood vessel. By impregnating the stent with the drug, and by implanting the drug-impregnated stent into the target site, the medication can be administered locally. Since the stent is implanted and left at the target site in the blood vessel over a prolonged time without obstructing the blood flow, it can be used as an LDDS which guarantees sufficient pharmaceutical effect over a prolonged time period.

Meanwhile, the stent clinically used at present is almost formed of metal without exception.

With metal, it is only possible to deposit a drug on its surface, while it is not possible to impregnate the metal itself with the drug. Among the methods for depositing a drug on a metal stent, there are, for example, a coating method, a bonding method and a method of covering the stent with a polymer sheet impregnated with the drug. In case the drug is deposited on the metal stent by coating or bonding, there is presented a problem that the drug itself becomes peeled off from the stent surface. It is also difficult to have a quantity of the drug sufficient to manifest its pharmaceutical effect deposited on the stent surface.

With the method of covering the stent with a polymer sheet, the polymer sheet impregnated with a drug needs to be prepared at a high temperature, thus possibly detracting from the pharmaceutical effect of the drug.

In LDDS, it is necessary to control the content of the drug, the amount of released drug per unit time and the releasing time. In order to prevent acute closure or re-stenosis by LDDS more effectively, such control is desirable that the effective concentration of the drug at the target site in the blood vessel be maintained and that the drug be released for a predetermined time to the blood vessel and into the blood.

DISCLOSURE OF THE INVENTION

It is therefore an object of the present invention to provide a luminal stent, in which a stent formed of a biodegradable polymer material is used as an LDDS member, a drug with sufficient pharmaceutical effect is impregnated in the stent formed of a biodegradable polymer material, without losing the pharmaceutical effect, the stent can be implanted and left at a local area at the target site in the blood vessel, without the drug becoming peeled off from the stent surface, and in which the drug of the effective concentration can be released for a required duration. It is another object of the present invention to provide a manufacturing method for the luminal stent.

For accomplishing the above object, the present invention provides a luminal stent, introduced into the blood vessel, wherein the stent is formed of a biodegradable polymer material to the shape of a tube, and the biodegradable polymer material becomes swollen to be impregnated with a drug.

The present invention also provides a luminal stent, wherein the biodegradable polymer material and the drug are exposed to a supercritical fluid for a predetermined time to permit swelling of the biodegradable polymer material and allow impregnation of this swollen biodegradable polymer material with the drug.

The drug impregnated in the biodegradable polymer material is selected to exhibit an anti-thrombotic effect and/or an intimal hyperplesia suppressing effect.

The biodegradable polymer material used may be an aliphatic polyester, a fatty acid anhydride, an aliphatic polycarbonate, polyphosphasen or a copolymer containing at least one of them.

The present invention also provides a luminal stent in which a layer of a biodegradable polymer material is further provided on the surface of a stent formed of a biodegradable polymer material, which is swollen and impregnated with a drug, such as to control the release rate of the drug impregnated into the biodegradable polymer layer forming the stent.

The present invention also provides a luminal stent in which a biodegradable polymer material containing a drug is coated once or several times on the surface of the stent, formed of a biodegradable polymer material, which is swollen and impregnated with the drug, to form plural biodegradable polymer layers containing a drug.

The biodegradable polymer layer, formed on the stent surface, is an aliphatic polyester, a fatty acid anhydride, an aliphatic polycarbonate, polyphosphasen or a copolymer containing at least one of them.

The biodegradable polymer layer, deposited on the stent surface, contains a drug. The drug used is selected to exhibit an anti-thrombotic effect.

On the stent surface, there may be formed at least one biodegradable polymer layer containing a drug and at least one biodegradable polymer layer.

In the plural biodegradable polymer layers, formed on the stent surface, there may also be contained drugs having respective different pharmaceutical effects.

The present invention provides a luminal stent in which the biodegradable polymer material is swollen and impregnated with a sufficient quantity of the drug.

With the luminal stent, according to the present invention, a sufficient quantity of the drug is impregnated with no loss of its pharmaceutical effect or no risk of peeling, thereby enabling a required quantity of the drug to be released continuously for a required duration to the wall of the blood vessel an into the blood flow.

With the luminal stent, according to the present invention, the drug impregnated into the inside of the stent is released with progress in the degradation of the biodegradable polymer material, forming the stent, thus enabling the drug to be released positively to the target site in the blood vessel carrying the stent.

By forming a further biodegradable polymer layer on the stent surface, it becomes possible to control the release rate of the drug into the blood, impregnated in the inside of the stent.

By having a drug contained in the further biodegradable polymer layer provided on the stent surface, plural drugs can be released at different timings into the blood. For example, by having the drug having the anti-thrombotic effect, contained in the biodegradable polymer layer, and by having the drug having the intimal hyperplesia suppressing effect, impregnated into the biodegradable polymer layer forming the stent, the drug having the anti-thrombotic effect can first be released into the blood, and the drug having the intimal hyperplesia suppressing effect can be released later.

Meanwhile, the drug can be impregnated into the swollen biodegradable polymer material, not as yet formed into a stent, then the resultant biodegradable polymer material is formed into a stent. Similarly, the biodegradable polymer layer or the biodegradable polymer layer containing the drug may be formed on the surface of the biodegradable polymer material not as yet formed into the stent, and the biodegradable polymer material, now provided with the biodegradable polymer layer, may then be formed into the stent.

Other objects, features and advantages of the present invention will become more apparent from reading the embodiments of the present invention as shown in the drawings.

BEST MODE FOR CARRYING OUT THE INVENTION

Figure 1:
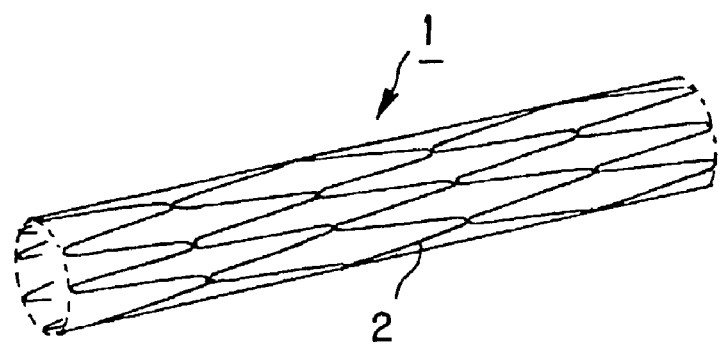
FIG. 1 is a perspective view showing an instance of a luminal stent according to the present invention.

Referring to the drawings, the luminal stent for the blood for blood vessel according to the present invention, and the method for manufacturing the stent, are now explained in detail.

The luminal stent, according to the present invention, is a fiber or a sheet of a biodegradable polymer material, which is formed into a tube so as to be implanted and left at a preset site in the blood vessel. The biodegradable polymer material, forming the stent, is swollen, and a drug, exhibiting an anti-thrombotic or intimal hyperplesia suppressing effect, is impregnated in this swollen biodegradable polymer material.

A luminal stent 1 according to the present invention is formed by a fiber 2 of a biodegradable polymer, shown in FIG. 1, with the fiber 2 being bent in consecutive V shapes in a zigzag pattern to form a strip which then is wound spirally to form into a cylindrical or a tubular shape, in particular a cylinder.

Figure 2:
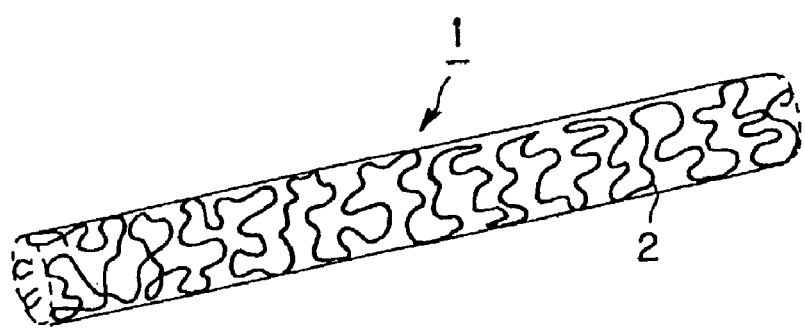
FIG. 2 is a perspective view showing another instance of a luminal stent according to the present invention.
Figure 3:
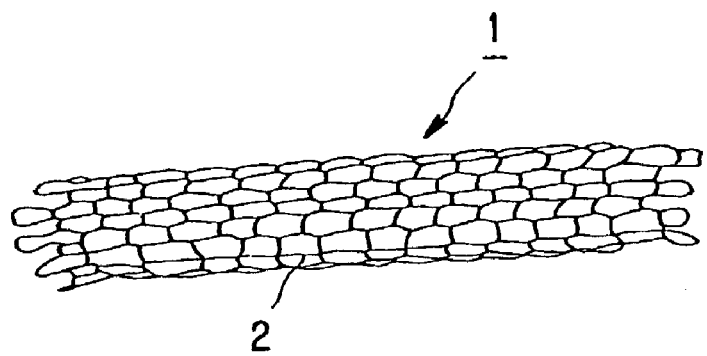
FIG. 3 is a perspective view showing still another instance of a luminal stent according to the present invention.
Figure 4:
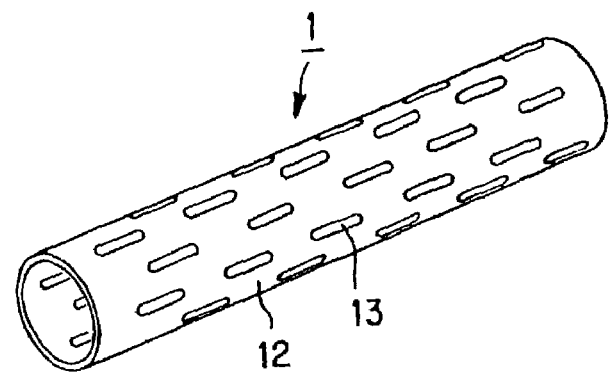
FIG. 4 is a perspective view showing yet another instance of a luminal stent according to the present invention.

As another instance of the luminal stent 1, the fiber 2 of the biodegradable polymer is formed in a non-woven non-knitted state into a cylinder or a tube, in particular a cylinder, as shown in FIG. 2. As further instances of the luminal stent 1, a sole fiber 2 of a biodegradable polymer is woven into a cylindrical shape, as shown in FIG. 3, or a sheet 12 of a biodegradable polymer is formed into a cylindrical or tubular shape, in particular a cylinder, as shown in FIG. 4. In the latter stent 1, plural through-holes 13 are bored at pleasure in the sheet 12 in order to impart flexibility to the sheet 12.

This stent 1 is formed by the fiber 2 or the sheet 12 of the biodegradable polymer material, so that the stent 1, while keeping its shape for a certain time period after it is implanted and left in the blood vessel of the living body, is degraded in about several months.

As this biodegradable polymer material, an aliphatic polyesters, aliphatic acid anhydrides, aliphatic polycarbonates, polyphosphasen or a copolymer containing at least one of them, may be used.

More specifically, one or more materials selected from the group of poly-L-lactic acid (PLLA), polyglycolic acid, polyglactin, polydioxanone, polyglyconate, ε-caprolactone, polylactic acid-ε-caprolactone copolymer, polyglycolic acid-ε-caprolactone copolymer, is used.

As the biodegradable polymer material, which forms the fiber or the sheet, PLLA, for example, is used. PLLA can be manufactured on lactic acid fermentation of natural cereals, and is a material having excellent biocompatibility. For this reason, the stent, formed using the fiber or sheet of PLLA, is not harmful to the human body.

When the biodegradable polymer material is used as fiber, the fiber can be in the form of a filament. The filament used is preferably an uninterrupted monofilament which is uniformly degraded in the living body.

As the drug to be impregnated in the swollen stent, it is possible to use a drug exhibiting anti-thrombotic effects, such as heparin or ticlopidine, or a drug exhibiting intimal hyperplesia suppressing effect, such as tranilast, pemirolast or carcinostatic agent.

If the swelling temperature of the biodegradable polymer is higher than the thermal decomposition temperature of the drug, the drug tends to be thermally decomposed at a time earlier than the polymer impregnated with the drug, thus detracting from the pharmaceutical effect of the drug. Thus, the swelling temperature of the biodegradable polymer must be lower than the thermal decomposition temperature of the drug so as not to detract from the pharmaceutical effect of the drug.

The stent, formed from the above-mentioned biodegradable polymer material is swollen by being exposed, along with the drug, to a supercritical fluid for a predetermined time. The luminal stent according to the present invention is produced by the drug being impregnated in this swollen stent.

It is noted that, if the drug impregnated is only sparingly soluble in the supercritical fluid, the quantity of the drug that can be impregnated may be increased by adding solvents such as water or ethanol.

A specified method for swelling the stent formed of the biodegradable polymer material, using the supercritical fluid, and for having the drug impregnated into this swollen stent, is hereinafter explained.

Although the instance of employing $CO_2$ as the supercritical fluid is explained here, any other suitable material than $CO_2$, exhibiting biocompatibility, such as $H_2O$, may also be used.

Figure 5:
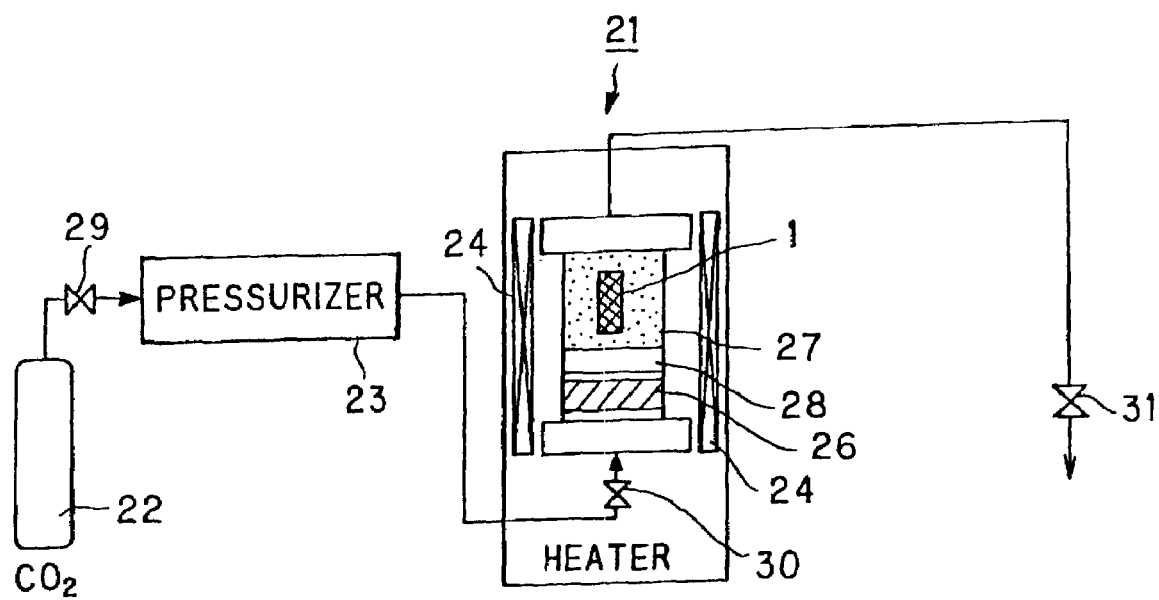
FIG. 5 is a block diagram showing an apparatus used for causing the stent of the present invention to be impregnated with a drug.

For swelling the stent formed of the biodegradable polymer material, using the supercritical fluid to allow impregnation with the drug, a device 21, constructed as shown for example in FIG. 5, may be used. This device 21 includes a $CO_2$ bomb 22, a pressurizer 23, for pressurizing $CO_2$, a heater 24, for warming $CO_2$, and a reaction chamber 27 for reacting $CO_2$ in the supercritical state, stent 1 and a drug 26. First, the stent 1 of any of the above-mentioned types and the drug 26 are charged into a reaction chamber 27. At this time, the stent 1 and the drug 26 are separated from each other by a porous filter 28 to prevent mixing.

A first valve 29 then is opened to discharge $CO_2$ from the $CO_2$ bomb 22. The discharged $CO_2$ is pressurized by pressurizer 23. A second valve 30 is opened to inject the pressurized $CO_2$ into the inside of the reaction chamber 27. It is necessary to set the pressure for injected $CO_2$ to a value higher than the critical pressure for $CO_2$ and a value lower than the pressure of deterioration of the material of the stent 1. When the stent 1 is formed by a fiber of the biodegradable polymer, the pressure of the injected $CO_2$ is preferably the pressure of maintaining the tensile strength of the fiber or smaller.

It is noted that the supercritical pressure of $CO_2$ used as this supercritical fluid is 7.38 MPa. It is therefore necessary to keep the pressure in the reaction chamber 27 to 7.38 MPa or higher. On the other hand, an experiment conducted by the present inventors has revealed that if, when the stent 1 is formed by a fiber of a biodegradable polymer material, the pressure within the reaction chamber 27 exceeds 24 MPa, the fiber of the biodegradable polymer material is lowered in tensile strength. That is, the pressure within the reaction chamber 27 must be 24 MPa or less.

By the heater 24, the temperature within the reaction chamber 27, injected $CO_2$, must be maintained at a temperature higher than the critical temperature of $CO_2$ and lower than the thermal decomposition temperature of the biodegradable polymer and the drug. The inside of the reaction chamber 27, injected $CO_2$, is preferably lower than the temperature of maintaining the tensile strength of the fiber of the biodegradable polymer material forming the stent 1.

The critical temperature of $CO_2$, used as the supercritical fluid, is 31.3° C. The temperature within the reaction chamber 27 must be set to 31.3° C. or higher. An experiment conducted by present inventors has revealed that if, when the stent 1 is formed of a fiber of PLLA, and the temperature becomes higher than 140° C., the tensile strength of the PLLA fiber is deteriorated. It is therefore necessary that the temperature within the reaction chamber 27 be lower than 140° C.

It is noted that $CO_2$ injected into the reaction chamber 27 is set to a pressure higher than the critical temperature and to a temperature higher than the critical temperature, and hence becomes a supercritical fluid. $CO_2$ in the state of the supercritical fluid is transmitted along with the drug 26 through a porous filter 28 so as to be diffused into the entire inner chamber of the reaction chamber 27. Hereby, the stent 1 is exposed to the drug 26 and to $CO_2$ in the state of the supercritical fluid. The stent 1, thus exposed to the drug 26 and to $CO_2$ in the state of the supercritical fluid for a predetermined time, becomes swollen, with the drug 26 being now impregnated in the so swollen stent 1.

Finally, a third valve 31 is opened to exhaust $CO_2$ within the reaction chamber 27 gradually to set the inside of the reaction chamber 27 open to atmosphere. The drug 26 is now fully impregnated in the stent 1 to complete the luminal stent according to the present invention.

In the above-described method, the fiber of the biodegradable polymer is first formed as a stent and subsequently swollen, and the drug is impregnated in this swollen stent. Alternatively, the fiber of the biodegradable polymer, not as yet formed to a stent, may first be swollen and the drug may then be impregnated into this fiber of the swollen biodegradable polymer, with the fiber of the biodegradable polymer being then formed into a cylindrical or tubular shape, in particular into a cylinder.

The present invention exploits the characteristics of the supercritical fluid in such a manner that the drug dissolved in the supercritical fluid is impregnated into the biodegradable polymer material based on the phenomenon of the polymer becoming swollen on absorption of a solvent, that is on the swelling caused to the biodegradable polymer.

The luminal stent according to the present invention is formed by fibers of the biodegradable polymer, so that it maintains its shape for a certain time period after it is implanted and left in the blood vessel of the living body. However, the stent is degraded in several months after it is implanted and left in the blood vessel of the living body, so that it may be caused to disappear in the tissue of the living body.

Since the luminal stent according to the present invention is formed of the biodegradable polymer material, which has become swollen and has impregnated with the drug in this state, the drug impregnated in the biodegradable polymer material is released into the blood vessel with degradation of the biodegradable polymer material. Thus, after the luminal stent of the present invention is implanted and left in the blood vessel, the drug can be continuously released into the blood vessel with degradation of the biodegradable polymer material forming the stent.

Meanwhile, if it is necessary to meticulously control the release into the blood vessel of the drug impregnated in the luminal stent, for example, if a large quantity of the drug is to be released in a short time, a drug-containing biodegradable polymer is coated or bonded to the stent surface to form a layer of the drug-containing biodegradable polymer on the stent surface. Additionally, for preventing a large quantity of the drug from being released from the stent, thereby remaining in the blood vessel, in a short time, that is for delaying the release of the drug impregnated in the stent into the blood vessel, it is also possible to form the layer of the biodegradable polymer material, formed only of the biodegradable polymer, on the surface of the stent formed of the drug-impregnated biodegradable polymer material.

The layer of the biodegradable polymer, whether or not containing the drug, may be formed by coating the stent surface with a solution, of the biodegradable polymer, such as poly-ε-caprolactone, in acetone etc, as solvent, or by immersing the stent in a solution of the biodegradable polymer.

The biodegradable polymer, containing or not containing the drug, may be provided on the stent surface in multiple layers. In this case, the layer(s) of the drug-containing biodegradable polymer and the layer(s) of the biodegradable polymer not containing the drug may be layered alternatively, or plural layers of the biodegradable polymer containing drugs exhibiting different pharmaceutical effects may be formed in multiple layers.

The layer(s) of the drug-containing biodegradable polymer material and the layer(s) of the biodegradable polymer not containing the drug may be formed not only on the stent surface, but also on the surface of the biodegradable polymer material not as yet formed into the stent.

An instance in which a layer of a biodegradable polymer material is further formed on the surface of a fiber of a biodegradable polymer, which has been impregnated with the drug by the swelling, is now specifically explained.

Figure 6:
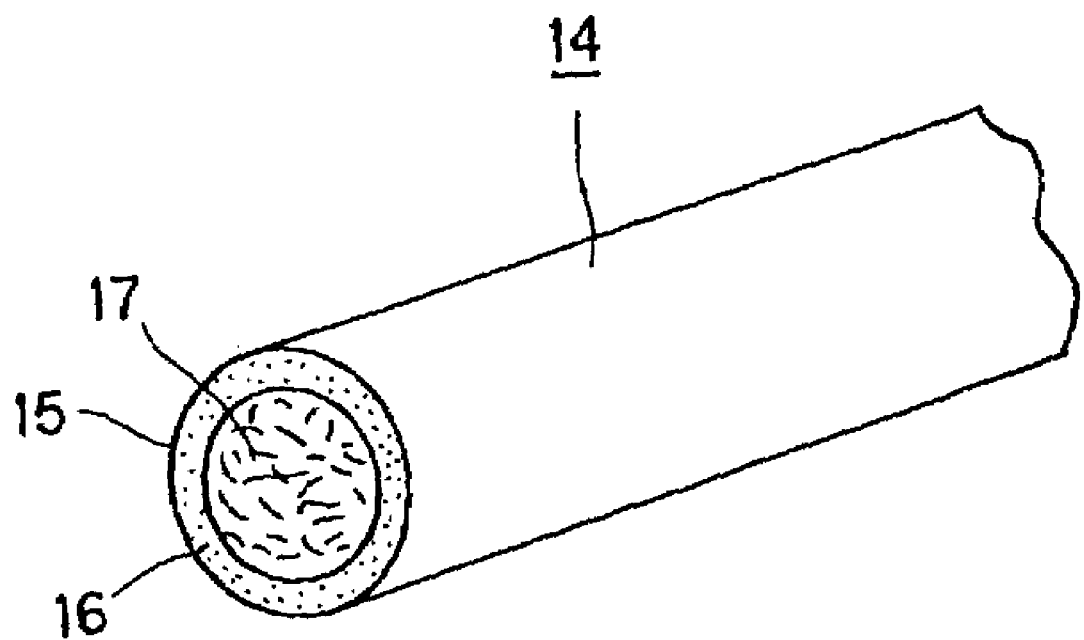
FIG. 6 is a cross-sectional view showing a fiber of a biodegradable polymer forming the luminal stent according to the present invention, with a drug-containing biodegradable polymer layer being formed on the surface of the stent-forming fiber.

A fiber 14 of the biodegradable polymer, forming this stent, is swollen, as shown in FIG. 6, to be impregnated with a drug 17. The surface of this fiber 14 is coated with a biodegradable polymer containing the drug 16 to provide the layer of the drug-containing biodegradable polymer 15. The drug 16, contained in the layer of the drug-containing biodegradable polymer 15, provided on the surface of the fiber 14, is released with degradation of the layer of the drug-containing biodegradable polymer 15. Subsequently, the drug 17, impregnated in the fiber 14 of the biodegradable polymer, is released. Meanwhile, the drug 16 applied to the surface of the fiber 14 may be the same as or different from the drug 17 impregnated in the fiber 14. That is, the drug released into the living body using the luminal stent according to the present invention may be selected appropriately. It is also possible to provide one or more layers of the drug-containing biodegradable polymer 15. By providing the layer(s) of the drug-containing biodegradable polymer 15 in this manner, one or more drugs may be impregnated in the stent, and it is possible to permit more strict control of the drug releasing time point or the quantity of the released drug, or different drugs can be released at the desired same time point. In particular, the thrombosis correlated with acute closure and intimal hyperplesia correlated with re-stenosis occur within a certain period following the operation of the balloon expansion or the stent implantation. Specifically, the thrombosis occurs immediately after the operation, while the intimal hyperplesia occurs in several weeks. That is, if, in FIG. 6, an anti-thrombotic agent and an intimal hyperplesia suppressing agent are used as the drugs 16 and 17, respectively, the anti-thrombotic agent may be released at an earlier time, and the intimal hyperplesia suppressing agent may then be released for a prolonged time period, thus enabling acute closure and the re-stenosis to be prevented with the same stent.

Figure 7:
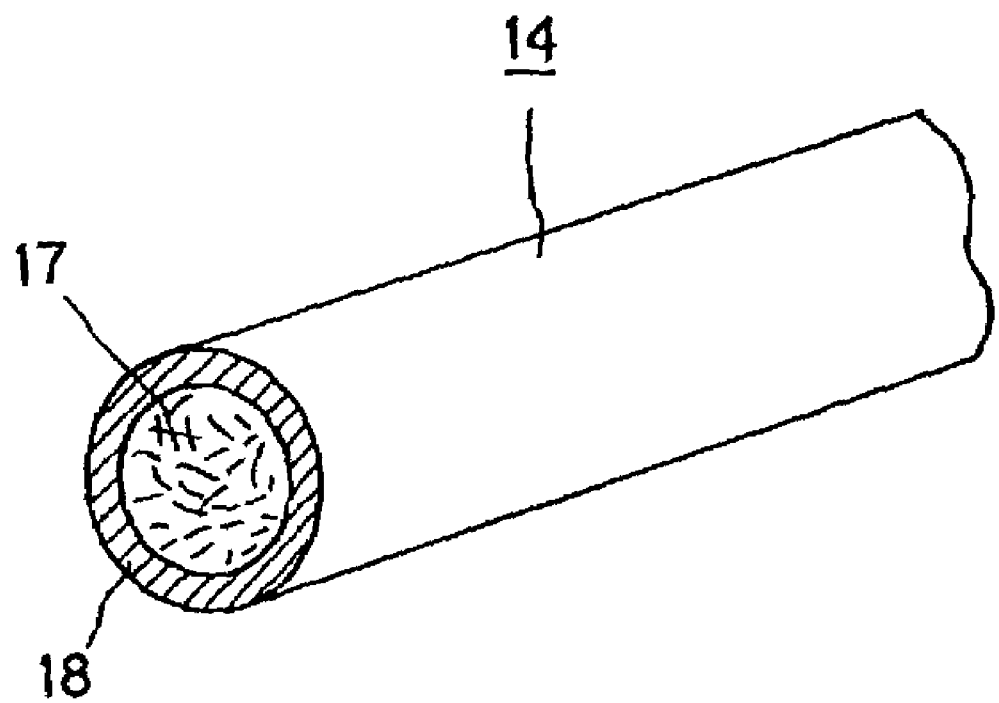
FIG. 7 is a cross-sectional view showing a fiber of a biodegradable polymer forming the luminal stent according to the present invention, with a biodegradable polymer being formed on the surface of the stent-forming fiber.

For retarding the rate of release of the drug impregnated in the stent, a further biodegradable polymer is coated on the surface of the fiber 14 of the biodegradable polymer, forming the stent, and which has become swollen to be impregnated with the drug 17, in order to form a layer of the biodegradable polymer 18, as shown in FIG. 7. By providing the layer of the biodegradable polymer 18 in this manner, the fiber 14 of the biodegradable polymer starts to be degraded, after degradation of the layer 18 of the biodegradable polymer to release the drug 17 impregnated, thereby retarding the start time of release of the drug 17.

On the surface of the fiber 14 of the biodegradable polymer, plural layers 15 of the biodegradable polymer containing the drug 16 and plural layers 18 of biodegradable polymer not containing the drug may be formed alternately. By this structure, the drug releasing time interval and/or the quantity of the released drug can be controlled more rigorously, or different drugs can be released at the desired time.

With the luminal stent of the present invention, the stent formed of the biodegradable polymer material is swollen and the drug can be impregnated in this swollen stent. Additionally, a sufficient quantity of the same or different drug may be impregnated in the outer periphery of the produced stent, without of the risk of the drug becoming detached therefrom. In addition, since the drug impregnated in the stent is released with degradation of the biodegradable polymer, it becomes possible to control the amount of release of the drug and the drug releasing time duration.

EXAMPLES

The present invention is now explained with reference to certain specified Examples based on experimental results.

Experimental Example 1

In the present experimental example, a plural number of fibers, each impregnated with a drug, were prepared, as the pressure and the temperature of $CO_2$ were changed, and the tensile strength was measured of each PLLA fiber.

Example 1

First, a PLLA fiber 170 μm in diameter and tranilast [N-(3,4-dimethoxy cinnamoyl) anthranilic acid], exhibiting intimal hyperplesia suppressing effect, were charged into a pressurized vessel 27 of the device 21 shown in FIG. 5. At this time, a porous filter was inserted into the space between the PLLA monofilament and tranilast. Meanwhile, tranilast is a drug effective in suppressing re-stenosis which occurs after the angioplasty.

Then, $CO_2$ was pressurized to 10 MPa by a pressurizer 23 and a second valve 30 was opened to inject it into the pressurized vessel 27. $CO_2$ pressurized in the pressurized vessel 27 was warmed to 80° C. to set it to a state of supercritical state fluid.

After the PLLA fiber and tranilast were exposed to $CO_2$ in the state of the supercritical fluid for two hours, $CO_2$ was gradually exhausted to set a state opened to atmosphere. This yields a tranilast-impregnated PLLA fiber.

Examples 2 to 13 and Comparative Examples 1 and 2

Using a method similar to the method used in Example 1, tranilast was impregnated in a PLLA fiber, under the conditions of the pressure and temperature shown in the following Table 1:

TABLE 1

| | pressure (MPa) | temperature (° C.) | tensile strength (N) |
|---|---|---|---|
| Ex. 1 | 10 | 80 | 8 |
| Ex. 2 | 13 | 80 | 7.9 |

TABLE 1-continued

|  | pressure (MPa) | temperature (° C.) | tensile strength (N) |
|---|---|---|---|
| Ex. 3 | 15 | 80 | 7.85 |
| Ex. 4 | 18 | 80 | 7.9 |
| Ex. 5 | 20 | 80 | 7.9 |
| Ex. 6 | 23 | 80 | 7.5 |
| Ex. 7 | 24 | 80 | 6.8 |
| Ex. 8 | 15 | 40 | 7.9 |
| Ex. 9 | 15 | 60 | 7.9 |
| Ex. 10 | 15 | 80 | 7.9 |
| Ex. 11 | 15 | 100 | 7.8 |
| Ex. 12 | 15 | 120 | 7.8 |
| Ex. 13 | 15 | 140 | 7.5 |
| Comp. Ex. 1 | 15 | 150 | 5 |
| Comp. Ex. 2 | 25 | 80 | 3 |

Comparative Example 3

Using a method similar to the method of Example 1, except not charging tranilast into the pressurized vessel, a PLLA fiber was exposed to $CO_2$ in the state of a supercritical fluid.

Comparative Examples 4 to 17

Using the method similar to the method used in Comparative Example 3, the PLLA fiber was exposed to $CO_2$ in the supercritical state, under the conditions of the pressure and temperature shown in the following Table 2:

TABLE 2

|  | pressure (MPa) | temperature (° C.) | tensile strength (N) |
|---|---|---|---|
| Comp. Ex. 3 | 10 | 80 | 8.2 |
| Comp. Ex. 4 | 13 | 80 | 8.1 |
| Comp. Ex. 5 | 15 | 80 | 8.1 |
| Comp. Ex. 6 | 18 | 80 | 8.1 |
| Comp. Ex. 7 | 20 | 80 | 7.9 |
| Comp. Ex. 8 | 23 | 80 | 7.6 |
| Comp. Ex. 9 | 24 | 80 | 6.7 |
| Comp. Ex. 10 | 15 | 40 | 7.85 |
| Comp. Ex. 11 | 15 | 60 | 8 |
| Comp. Ex. 12 | 15 | 80 | 8.1 |
| Comp. Ex. 13 | 15 | 100 | 8. |
| Comp. Ex. 14 | 15 | 120 | 7.9 |
| Comp. Ex. 15 | 15 | 140 | 7.4 |
| Comp. Ex. 16 | 15 | 150 | 4.5 |
| Comp. Ex. 17 | 25 | 80 | 3 |

A tensile test was conducted on the fibers of PLLA obtained by Examples 1 to 13 and Comparative Examples 1 to 17 to find the tensile strength. The results are shown in the above Tables 1 and 2 and in FIGS. 8 and 9.

Figure 8:
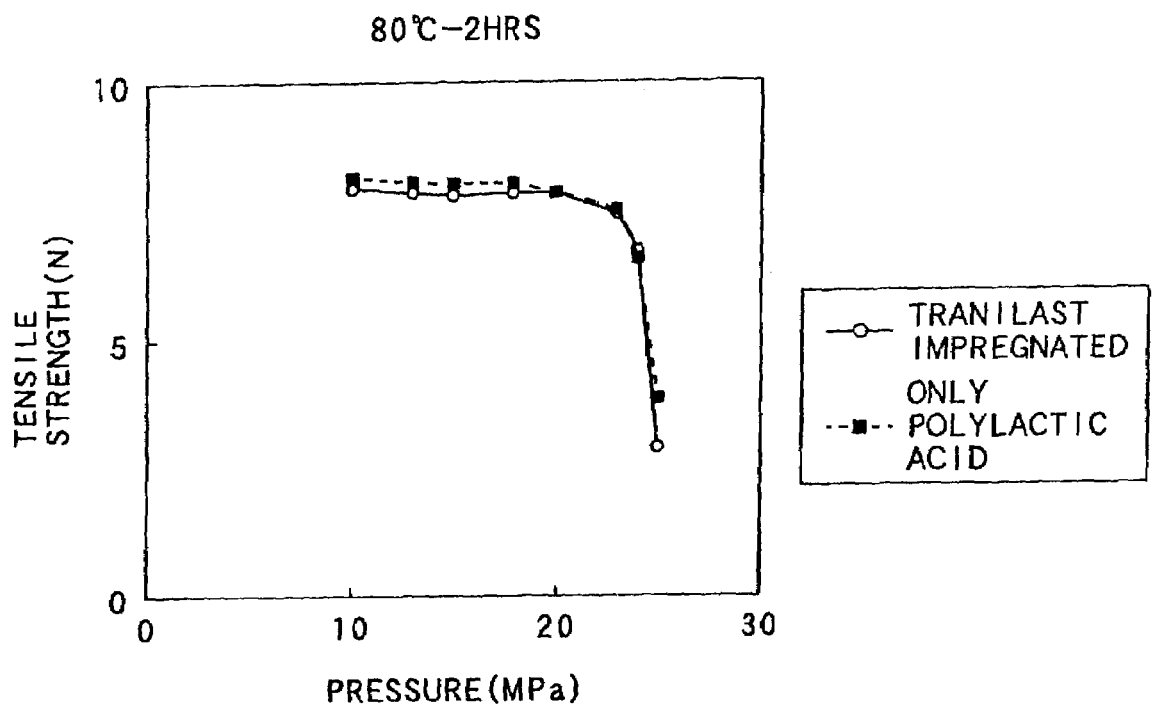
FIG. 8 is a graph showing the relationship between the pressure of $CO_2$ rendered fluid in the supercritical state and the tensile strength of a fiber of PLLA.

From FIG. 8 and Table 1, it is seen that, with the Examples 1 to 13 in which $CO_2$ is a supercritical fluid, with the pressure of 10 to 24 MPa, the tensile strength of the PLLA fiber is 6.8N or higher, whereas, with the Comparative Example 2 in which $CO_2$ is the supercritical fluid, with the pressure of 25 MPa, the tensile strength is 3N. That is, if tranilast is impregnated in the PLLA fiber, with use of $CO_2$, which is a supercritical fluid at a pressure higher than 24 MPa, the tensile strength is lowered.

FIG. 8 shows an example in which a PLLA fiber is exposed to the supercritical fluid $CO_2$ at 80° C. for two hours, as the pressure is changed.

Figure 9:
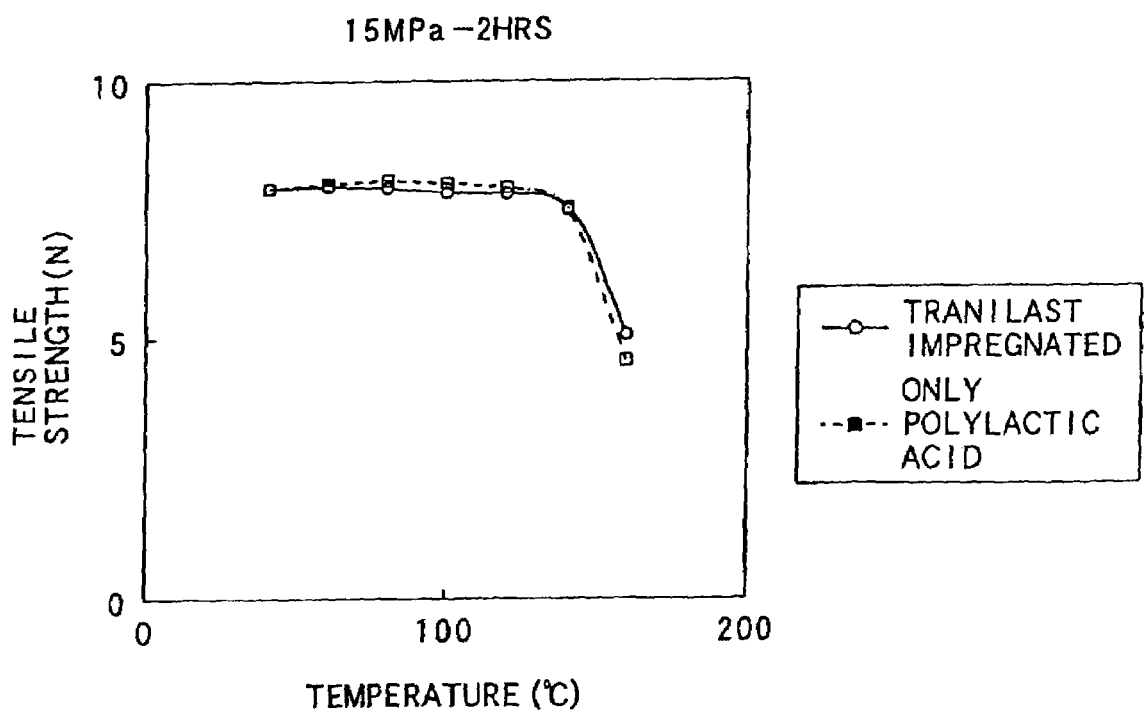
FIG. 9 is a graph showing the relationship between the temperature of $CO_2$ rendered fluid in the supercritical state and the tensile strength of a fiber of PLLA.

It may be seen from FIG. 9 and Table 1 that, in Examples 1 to 13 where $CO_2$ is in the state of a supercritical fluid at a temperature of 40 to 140° C., the tensile strength of the PLLA fiber is 6.8N or higher, whereas, in Comparative Example 1 where $CO_2$ is in the state of a supercritical fluid at a temperature of 150° C., the tensile strength is 5N. That is, if, with use of $CO_2$ in the state of a supercritical fluid at a higher temperature of 140° C., tranilast is impregnated in a PLLA fiber, the tensile strength is lowered. Thus, it has been shown that, if tranilast is impregnated in the PLLA fiber, using $CO_2$, which is in the supercritical fluid at 7.38 to 24 MPa and 31.3 to 140° C., a sufficient tensile strength of the PLLA fiber may be maintained.

FIG. 9 shows a case in which the PLLA fiber is exposed for two hours to a supercritical fluid $CO_2$, with the pressure of 15 MPa, as the temperature is changed.

Experimental Example 2

In the experimental example 2, a plural number of luminal stents, formed of plural biodegradable polymer material, in particular plural fibers of biodegradable polymer, in which the drug was impregnated as the pressure and the temperature of $CO_2$ were varied, were formed, and measurements were made of the amount of the drug for each of these stents.

Example 14

A PLLA monofilament, 170 μm in diameter, was bent into a zigzag pattern and wound into a cylinder, as shown in FIG. 1, to form a cylindrically-shaped stent 1, with a diameter of approximately 3.5 mm and a length of approximately 12 mm.

This stent 1 and tranilast were charged into a pressurized vessel 27 of the device 21 shown in FIG. 5. At this time, a porous filter was inserted into the space between the PLLA monofilament and tranilast.

Then, $CO_2$ was pressurized to 10 MPa by a pressurizer 23 and the second valve 30 was opened to inject $CO_2$ into the inside of the pressurized vessel 27. The $CO_2$ pressurized in the pressurized vessel 27 was warmed to 80° C. to set the state of a supercritical fluid.

Examples 15 to 25

In the same way as in Example 14, tranilast was impregnated in the stent, under pressure and temperature conditions shown in Table 3.

Of the stents, obtained in Examples 14 to 25, the amount of tranilast was measured using a high performance liquid chromatography. The results are shown in Table 3 and FIGS. 10 and 11.

Figure 10:
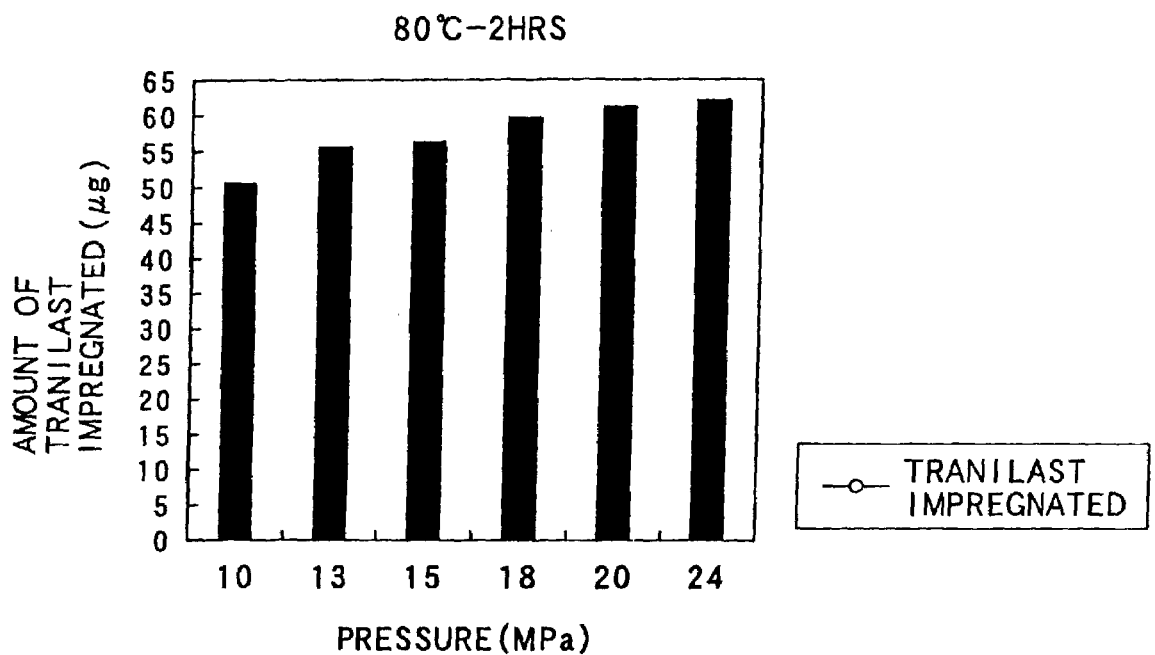
FIG. 10 is a graph showing the relationship between the pressure of $CO_2$ rendered fluid in the supercritical state and the amount of the drug impregnated in the stent.

FIG. 10 shows an instance where the PLLA fiber was exposed for two hours to the supercritical fluid $CO_2$, at 80° C., as the pressure was changed.

Figure 11:
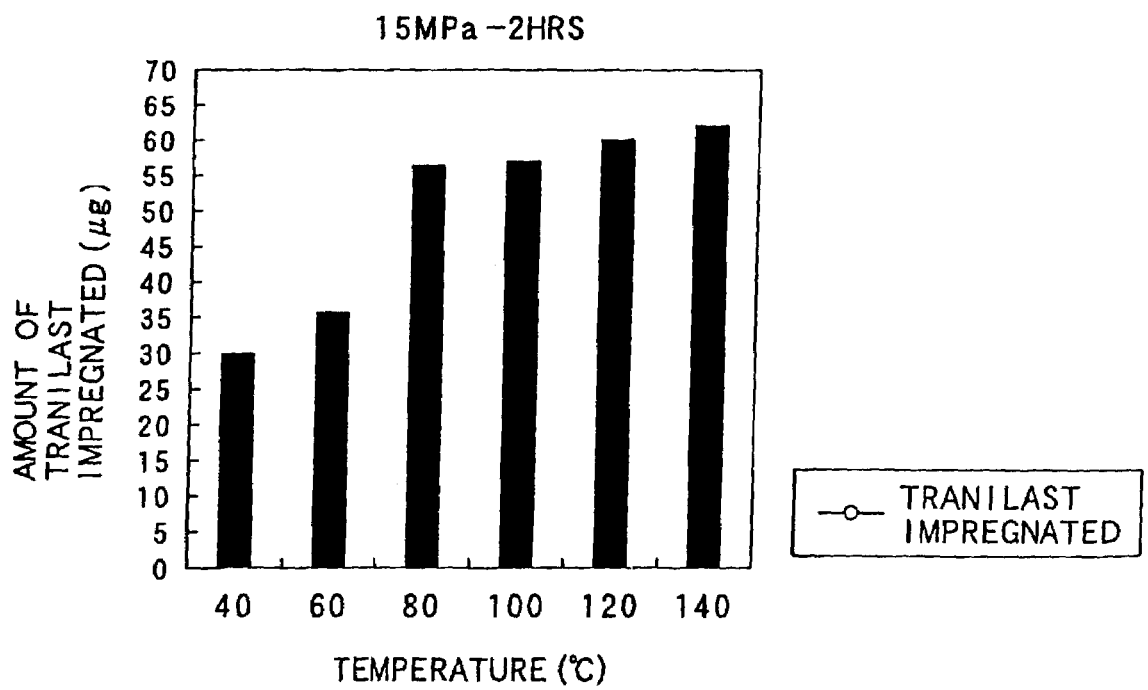
FIG. 11 is a graph showing the relationship between the temperature of $CO_2$ rendered fluid in the supercritical state and the amount of the drug impregnated in the stent.

FIG. 11 shows an instance where the PLLA fiber was exposed for two hours to the supercritical fluid $CO_2$, at a pressure of 15 MPa, as the temperature was changed.

TABLE 3

|  | pressure (Mpa) | temperature (° C.) | amount of tranilast impregnated |
|---|---|---|---|
| Ex. 14 | 10 | 80 | 50.2 |
| Ex. 15 | 13 | 80 | 55.3 |
| Ex. 16 | 15 | 80 | 56.1 |
| Ex. 17 | 18 | 80 | 59.3 |
| Ex. 18 | 20 | 80 | 60.7 |
| Ex. 19 | 24 | 80 | 61.5 |
| Ex. 20 | 15 | 40 | 30 |
| Ex. 21 | 15 | 60 | 35.4 |
| Ex. 22 | 15 | 80 | 56.6 |
| Ex. 23 | 15 | 100 | 57.2 |

TABLE 3-continued

| | pressure (Mpa) | temperature (° C.) | amount of tranilast impregnated |
|---|---|---|---|
| Ex. 24 | 15 | 120 | 60.3 |
| Ex. 25 | 15 | 140 | 62.0 |

As may be seen from FIGS. 10 and 11 and table 3, it has been shown that a tranilast-impregnated luminal stent according to the present invention can be prepared by exposing the stent and tranilast to $CO_2$ as the supercritical fluid. It is noted that tranilast was impregnated in the stent, under these temperature conditions, without undergoing thermal decomposition. This is brought about by the fact that $CO_2$ was low in critical temperature such that tranilast could be impregnated in the stent without being exposed to higher temperatures. It may be said that $CO_2$ having a low critical temperature is usable in conjunction with many different drugs.

From Examples 14 to 25, it has also been shown that the quantity of tranilast impregnated in the stent depends on the pressure and temperature of the supercritical fluid $CO_2$, and that, in particular, if the temperature at which $CO_2$ is made into a supercritical fluid is high, the quantity of tranilast impregnated is increased.

INDUSTRIAL APPLICABILITY

With the luminal stent, according to the present invention, described above, the stent formed of the biodegradable polymer material is swollen, and the drug is impregnated in this swollen stent, so that a sufficient quantity of the drug can be impregnated without the risk of the drug becoming disengaged from the stent, with the consequence that the drug can be continuously released into the blood vessel over a prolonged period of time.

Moreover, according to the present invention, a further biodegradable polymer layer is formed on the surface of the drug-impregnated biodegradable polymer material, forming the stent, or on the surface of the stent formed of the drug-impregnated biodegradable polymer material, it is possible to control the time of release of the drug, impregnated in the stent, into the living body, such that the drug can be released at the most desirable time.

Furthermore, by forming a biodegradable polymer layer containing a further drug on the surface of the biodegradable polymer material or on the surface of the stent formed using this biodegradable polymer material, drugs of plural different sorts can be released into the living body at the controlled timing. Consequently, the drugs released into the living body can be controlled freely so that plural sorts of the drugs can be released at a desired sequence.

The invention claimed is:

1. A method for manufacturing a luminal stent comprising:
permitting swelling of a stent formed of a biodegradable polymer material by a supercritical fluid in a pressurized vessel to allow impregnation of said biodegradable polymer material with a drug.

2. The method for manufacturing a luminal stent according to claim 1 wherein the pressure in said pressurized vessel is higher than the critical pressure of said supercritical fluid and lower than the pressure under which said biodegradable polymer material is deteriorated.

3. The method for manufacturing a luminal stent according to claim 1 wherein the temperature in said pressurized vessel is higher than the critical temperature of said supercritical fluid, while and lower than the thermal decomposition temperature at which said biodegradable polymer material and said drug are thermally decomposed.

4. A stent material for forming a luminal stent introduced into a blood vessel, wherein
said stent material is a biodegradable polymer material which is swollen and impregnated with a drug and on the surface of which a biodegradable polymer layer is layered;
wherein said biodegradable polymer material is composed of one or more high-melting point polymers or copolymers selected from a group comprising poly-L-lactic acid, polyglycolic acid, polyglactin, polydioxanone, polyglyconate.

5. The stent material for forming a luminal stent according to claim 4 wherein said biodegradable polymer material is an aliphatic polyester, a fatty acid anhydride, an aliphatic polycarbonate, polyphosphasen or a copolymer containing at least one of them.

6. The stent material for forming a luminal stent according to claim 4 wherein the biodegradable polymer material is a fiber.

7. The stent material for forming a luminal stent according to claim 6 wherein the fiber of the biodegradable polymer material is an uninterrupted monofilament.

8. The stent material for forming a luminal stent according to claim 4 wherein the fiber of the biodegradable polymer material is in a form of a sheet.

9. The stent material for forming a luminal stent according to claim 4 wherein the biodegradable polymer layered on the surface of said biodegradable polymer material contains an aliphatic polyester, a fatty acid anhydride, an aliphatic polycarbonate, polyphosphasen or a copolymer containing at least one of them.

10. The stent material for forming a luminal stent according to claim 4 wherein the drug impregnated in said biodegradable polymer material has an anti-thrombotic effect and/or an intimal hyperplesia suppressing effect.

11. The stent material for forming a luminal stent according to claim 4 wherein said biodegradable polymer layer contains a drug.

12. The stent material for forming a luminal stent according to claim 4 wherein said drug has anti-thrombotic effect.

13. The stent material for forming a luminal stent according to claim 4 wherein at least one biodegradable polymer layer containing a drug and at least one biodegradable polymer layer are formed on the surface of said stent material.

14. The stent material for forming a luminal stent according to claim 4 wherein drugs having different pharmaceutical effects are contained in plural biodegradable polymer layers formed on the surface of said stent material.

15. The stent material for forming a luminal stent according to claim 4 wherein the biodegradable polymer layered on the surface of said biodegradable polymer material is composed of one or more high-melting point polymers or copolymers selected from a group comprising poly-L-lactic acid, polyglycolic acid, polyglactin, polydioxanone, polyglyconate.

* * * * *